US010416114B2

(12) United States Patent
Chen et al.

(10) Patent No.: US 10,416,114 B2
(45) Date of Patent: Sep. 17, 2019

(54) STRUCTURES AND MANUFACTURE METHOD OF ELECTROCHEMICAL UNITS

(71) Applicant: INDUSTRIAL TECHNOLOGY RESEARCH INSTITUTE, Hsinchu (TW)

(72) Inventors: Jui-Chin Chen, Zhubei (TW); Pei-Jer Tzeng, Zhubei (TW); Tzu-Kun Ku, Hsinchu (TW); Yu-Chen Hsin, Zhubei (TW); Yiu-Hsiang Chang, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 302 days.

(21) Appl. No.: 15/352,242

(22) Filed: Nov. 15, 2016

(65) Prior Publication Data
US 2017/0343506 A1   Nov. 30, 2017

(30) Foreign Application Priority Data
May 26, 2016   (TW) .............................. 105116407 A

(51) Int. Cl.
G01N 27/403   (2006.01)
G01N 27/417   (2006.01)
(Continued)

(52) U.S. Cl.
CPC ........... *G01N 27/417* (2013.01); *G01N 27/27* (2013.01); *G01N 33/4836* (2013.01);
(Continued)

(58) Field of Classification Search
CPC ............. G01N 33/4836; G01N 27/327; G01N 27/3272; G01N 27/403
See application file for complete search history.

(56) References Cited

U.S. PATENT DOCUMENTS 4,650,288 A * 3/1987 White ................... G02F 1/0102
                                                    345/107
5,437,999 A * 8/1995 Diebold ................. C12Q 1/001
                                                    204/403.11
(Continued)

FOREIGN PATENT DOCUMENTS

CN   102954994 A   3/2013
TW      533305 B   5/2003
TW   200830565 A   7/2008

OTHER PUBLICATIONS

Taiwanese Office Action and Search Report, dated Sep. 30, 2017, for Taiwanese Application No. 105116407.
(Continued)

*Primary Examiner* — Alexander S Noguerola
(74) *Attorney, Agent, or Firm* — Birch, Stewart, Kolasch & Birch, LLP

(57) ABSTRACT

A structure of an electrochemical unit includes a substrate, a first metal layer disposed on the substrate, and an array of electrochemical cells disposed on the first metal layer. The array of the electrochemical cells includes a plurality of electrochemical cells. Each of the electrochemical cells includes the first metal layer disposed on the substrate, a first electrode disposed on the first metal layer, a polymer layer disposed on the substrate and adjacent to the first metal layer and the first electrode. A second metal layer is disposed on the polymer layer, and a second electrode is disposed on the second metal layer. A pore is constituted between the polymer layers of every the two electrochemical cells. A cavity located above the first electrode is defined between every the two electrochemical cells, wherein the cavity is communicated with the pore.

37 Claims, 16 Drawing Sheets

(51) Int. Cl.
*G01N 33/483* (2006.01)
*G01N 33/487* (2006.01)
*G01N 27/27* (2006.01)
*G01N 27/327* (2006.01)

(52) U.S. Cl.
CPC ..... *G01N 33/48721* (2013.01); *G01N 27/327* (2013.01); *G01N 27/403* (2013.01)

(56) References Cited

U.S. PATENT DOCUMENTS

| | | | |
|---|---|---|---|
| 5,863,400 | A | 1/1999 | Drummond et al. |
| 6,001,239 | A | 12/1999 | Douglas et al. |
| 6,428,665 | B1 | 8/2002 | Ilic et al. |
| 7,981,362 | B2 * | 7/2011 | Glezer ................ B01L 3/5085 422/50 |
| 2010/0025263 | A1 | 2/2010 | White et al. |
| 2014/0318957 | A1 * | 10/2014 | Abbott ................ G01N 27/403 204/400 |
| 2015/0129425 | A1 * | 5/2015 | Tsukada ............... G01N 27/327 204/403.14 |
| 2016/0168613 | A1 * | 6/2016 | Ayyub ............... G01N 27/3277 435/26 |

OTHER PUBLICATIONS

"Decoding DNA: Translating the Blueprint of Life", Oxford Nanopores: GridION, 2 sheets, http://decodingdna.yolasite.com/gridion.php, retrieved Nov. 2, 2016.

Allen J. Bard et al., "Electrochemical Methods: Fundamentals and Applications, 2nd Edition", John Wiley & Sons, Inc., 2001, Chapter 1, pp. 1-43, (45 sheets total).

James Clarke et al., "Continuous Base Identification for Single-molecule Nanopore DNA Sequencing", Nature Nanotechnology, 2009, vol. 4, pp. 265-270.

Tianyang Zheng et al., "Generation of Chip Based Microelectrochemical Cell Arrays for Long-term and High-resolution Recording of Ionic Currents through Ion Channel Proteins", Sensors and Actuators B: Chemical, 2014, vol. 205, pp. 268-275.

* cited by examiner

1

STRUCTURES AND MANUFACTURE METHOD OF ELECTROCHEMICAL UNITS

CROSS REFERENCE TO RELATED APPLICATIONS

This Application claims the priority of Taiwan Patent Application No. 105116407, filed on May 26, 2016, the entirety of which is incorporated by reference herein.

TECHNICAL FIELD

The disclosure relates to a structure and manufacture method of an electrochemical unit.

BACKGROUND

An electrochemical cell is formed by ion motion in a solution between an anode and a cathode, or electron movement in external metal wires between the anode and the cathode. For example, in an electroplating process of a semiconductor manufacturing process, ions in a solution are used to deposit a thin-film metal layer.

In an electrochemical cell, an external-linking external electrode is usually adopted to connect to a plurality of internal electrodes on a chip. The distance between the external electrode and the internal electrode is longer due to the external-linking external electrode. If the distance between the external electrode and the internal electrode is shortened, a potential drop (IR drop) caused by a solution between the electrodes can be reduced and the electrode field between the electrodes also can be improved to enhance ion motion resulting in electric current increasing.

In semiconductor manufacturing processes, if a cavity is formed by a bonding procedure, some problems such as poor bonding and alignment error may occur during the formation processes of the cavity. Especially, when the size of the electrochemical cell is reduced, these problems such as poor bonding and alignment error are more likely to be serious.

SUMMARY

A structure of an electrochemical unit is provided. The structure of the electrochemical unit comprises a substrate; a first metal layer disposed on the substrate; and an array of electrochemical cells disposed on the first metal layer, wherein the array of the electrochemical cells comprises a plurality of electrochemical cells, and each of the electrochemical cells comprises the first metal layer disposed on the substrate; a first electrode disposed on the first metal layer; a polymer layer disposed on the substrate and adjacent to the first metal layer and the first electrode; a second metal layer disposed on the polymer layer; and a second electrode disposed on the second metal layer.

A manufacture method of an electrochemical unit is provided. The manufacture method of an electrochemical unit comprises providing a substrate; and forming an array of electrochemical cells on the substrate, wherein the array of the electrochemical cells comprises a plurality of electrochemical cells, and the steps comprise forming a plurality of first electrodes on the substrate; forming a polymer layer on the first electrodes and the substrate; and forming a second electrode on the polymer layer.

A detailed description is given in the following embodiments with reference to the accompanying drawings.

2

BRIEF DESCRIPTION OF THE DRAWINGS

The present invention can be more fully understood by reading the subsequent detailed description and examples with references made to the accompanying drawings, wherein.

DETAILED DESCRIPTION

Figure 1A:
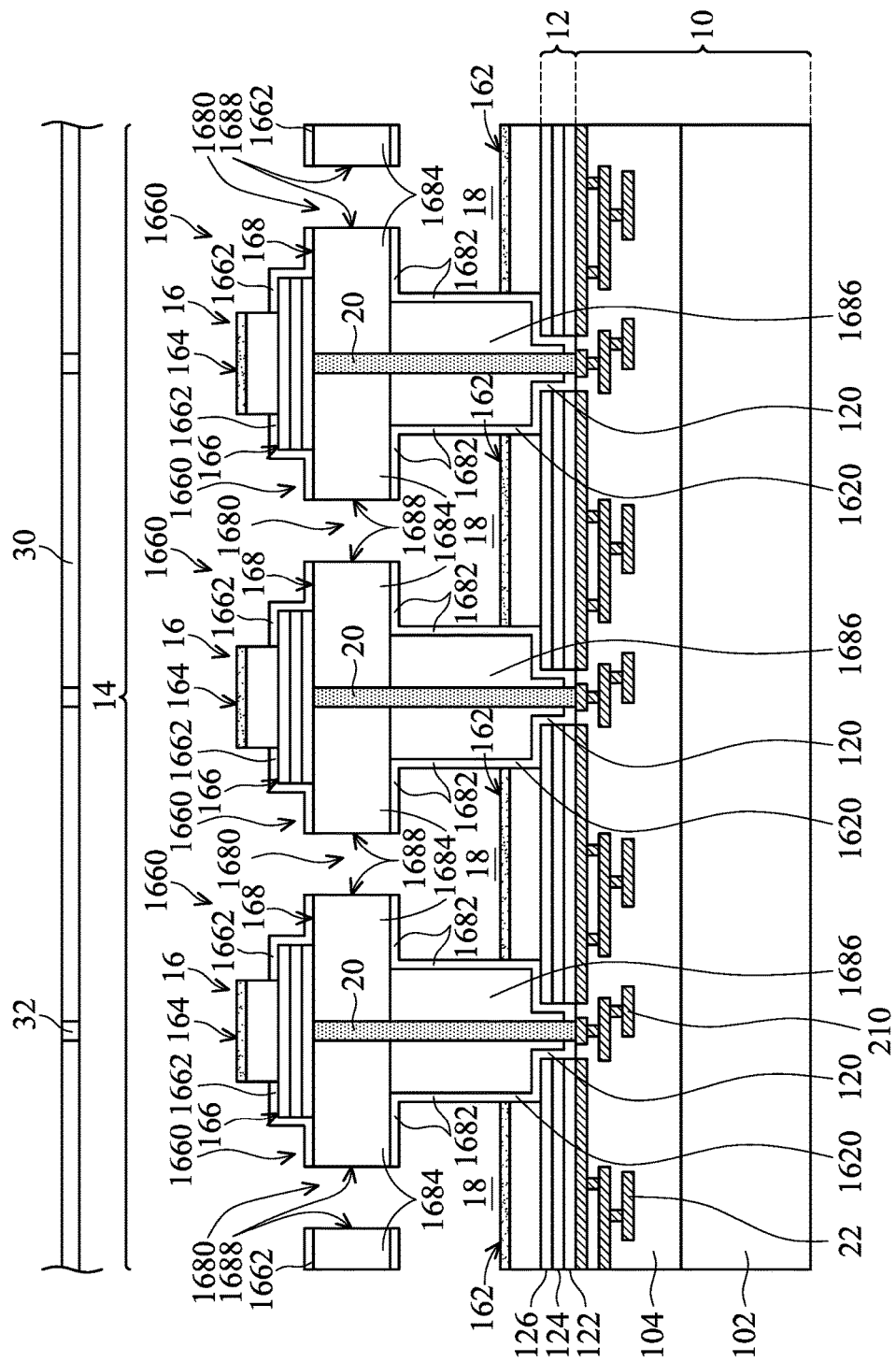
FIG. 1A is a cross-sectional view of a structure of an electrochemical unit in accordance with the first embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Referring to FIG. 1A, FIG. 1B, FIG. 2A and FIG. 2B, which are, respectively, a cross-sectional view of the first embodiment, a cross-sectional view of the second embodiment, a cross-sectional view of the third embodiment and a cross-sectional view of the fourth embodiment of a structure of an electrochemical unit of the disclosure, the structure of the electrochemical unit of the disclosure comprises a substrate 10, a first metal layer 12, and an array 14 of electrochemical cells. The first metal layer 12 is disposed on the substrate 10. The array 14 of the electrochemical cells is disposed on the first metal layer 12. The substrate 10 may comprise a silicon substrate 102 and an oxide layer or a nitride layer 104 having metal wires and active components. The oxide layer or the nitride layer 104 having metal wires and active components is disposed on the silicon substrate 102. The first metal layer 12 may comprise a stack of titanium 122, copper 124 and gold 126. The titanium 122 may be in contact with the oxide layer or the nitride layer 104 having metal wires and active components of the substrate 10. Other equivalent structures also belong to the scope of the disclosure.

In one embodiment, the first metal layer 12 may comprise chromium/nickel (Cr/Ni), chromium/gold (Cr/Au), titanium/copper (Ti/Cu), nickel/gold (Ni/Au), chromium/nickel/gold (Cr/Ni/Au), titanium/copper/gold (Ti/Cu/Au) or titanium/gold (Ti/Au).

The array 14 of the electrochemical cells comprises a plurality of electrochemical cells 16. Each of the electrochemical cells 16 comprises a first electrode 162, a second electrode 164, a second metal layer 166 and a polymer layer 168. The first electrode 162 may comprise silver/silver chloride. The first electrode 162 is disposed on the first metal layer 12. The bottom of the polymer layer 168 is disposed in an opening 1620 between the first electrodes 162 and in a first opening 120 between the first metal layers 12, and adjacent to the first electrodes 162 and the first metal layer 12. The polymer layer 168 may comprise polymer materials or oxide/nitride materials such as silicon oxide, silicon nitride or a multi-layered oxide/nitride film. The second electrode 164 is disposed on the second metal layer 166. The second metal layer 166 is disposed on the polymer layer 168. The second metal layer 166 may comprise a plurality of second openings 1660. The second metal layer 166 may comprise a stack of titanium, copper and gold. The titanium may be in contact with the polymer layer 168. The gold may be in contact with the second electrode 164.

In one embodiment, the second metal layer 166 may comprise chromium/nickel (Cr/Ni), chromium/gold (Cr/Au), titanium/copper (Ti/Cu), nickel/gold (Ni/Au), chromium/nickel/gold (Cr/Ni/Au), titanium/copper/gold (Ti/Cu/Au) or titanium/gold (Ti/Au). The second electrode 164 may comprise silver/silver chloride.

In one embodiment, each of the electrochemical cells 16 comprises the first metal layer 12 disposed on the substrate 10, the first electrode 162 disposed on the first metal layer 12, the polymer layer 168 disposed on the substrate 10 and adjacent to the first metal layer 12 and the first electrode 162. The second metal layer 166 is disposed on the polymer layer 168, and the second electrode 164 is disposed on the second metal layer 166. Therefore, the design of disposition of the second electrode 164 on the polymer layer 168 is to integrate the second electrode 164 into the electrochemical cell such that inconsistency of potential drop between the second electrode 164 (an external electrode) and a plurality of internal electrodes (the first electrodes 162) caused by solution is improved, and to shorten the distance between the first electrode 162 (an internal electrode) and the second electrode 164 (an external electrode), improving potential drop caused by an electrolyte solution. Additionally, poor bonding and alignment error caused by a bonding procedure in processes are also improved.

Figure 2A:
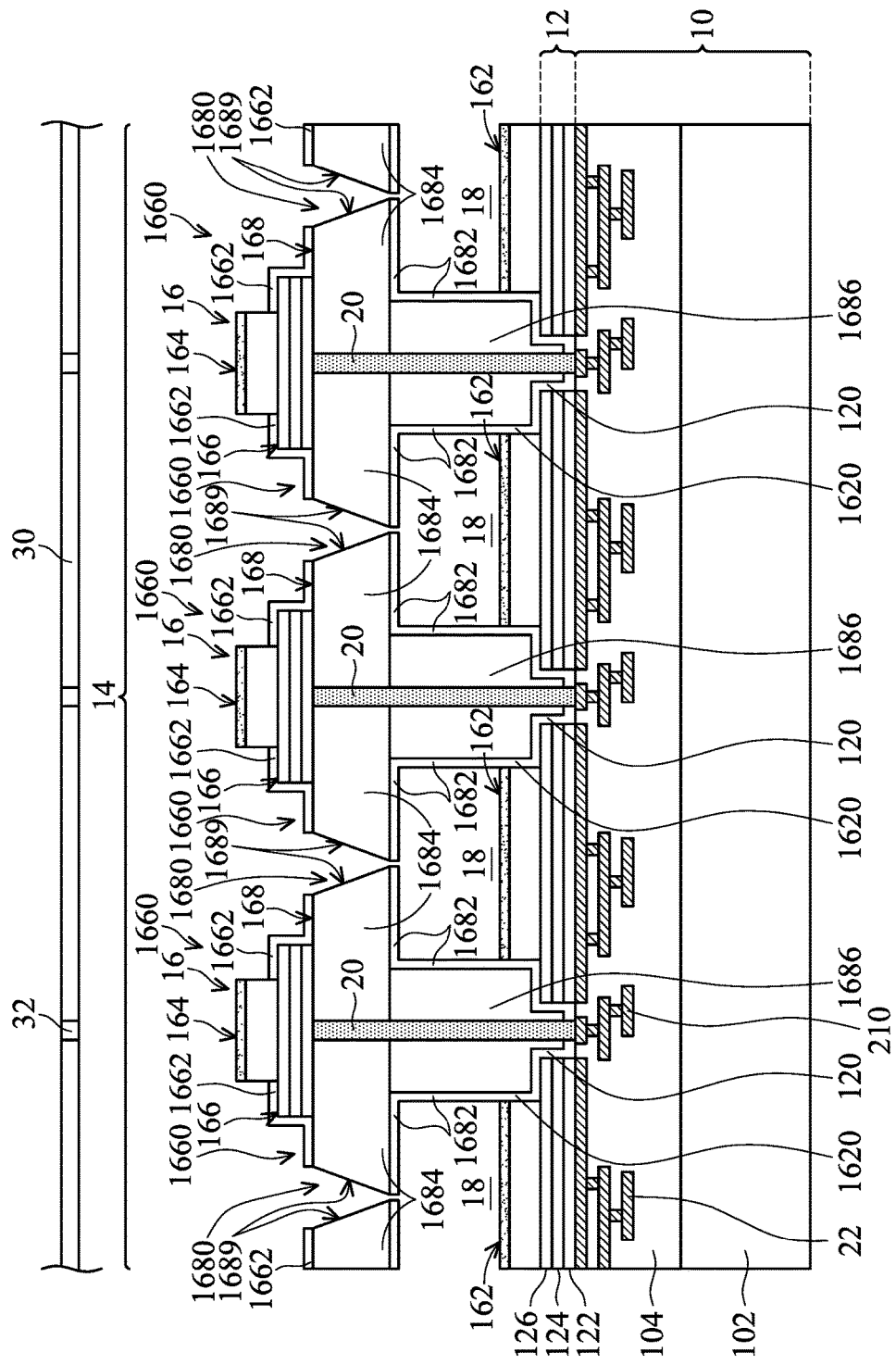
FIG. 2A is a cross-sectional view of a structure of an electrochemical unit in accordance with the third embodiment of the disclosure.

A pore 1680 is constituted between the polymer layers 168 of every the two electrochemical cells 16, and a cavity 18 located above the first electrode 162 is defined between every the two electrochemical cells 16. The cavity 18 is communicated with the second opening 1660 and the pore 1680. A protection layer or a stop layer 1682 may be formed on walls of the polymer layer 168 located at the periphery of the cavity 18 to protect the polymer layer 168. The protection layer or the stop layer 1682 is formed around the cavity 18, which is capable of increasing selection of materials of the cavity 18. Furthermore, the polymer layer 168 may be a T-shaped structure, as shown in FIGS. 1A and 2A. The polymer layer 168 may be a T-shaped structure formed of a horizontal portion 1684 and a vertical portion 1686. The horizontal portion 1684 and the vertical portion 1686 may be the same material or different materials.

Figure 1B:
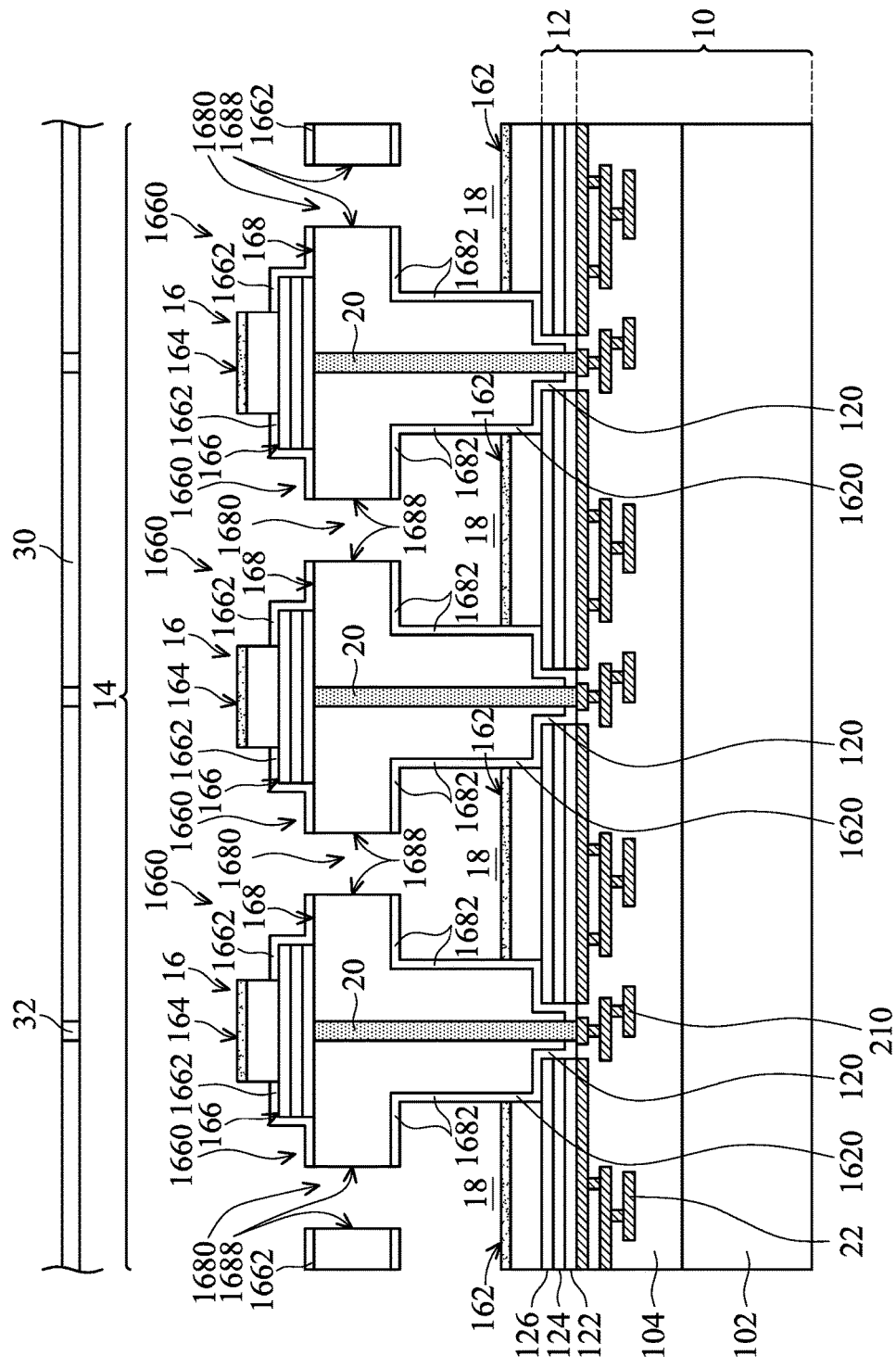
FIG. 1B is a cross-sectional view of a structure of an electrochemical unit in accordance with the second embodiment of the disclosure.
Figure 2B:
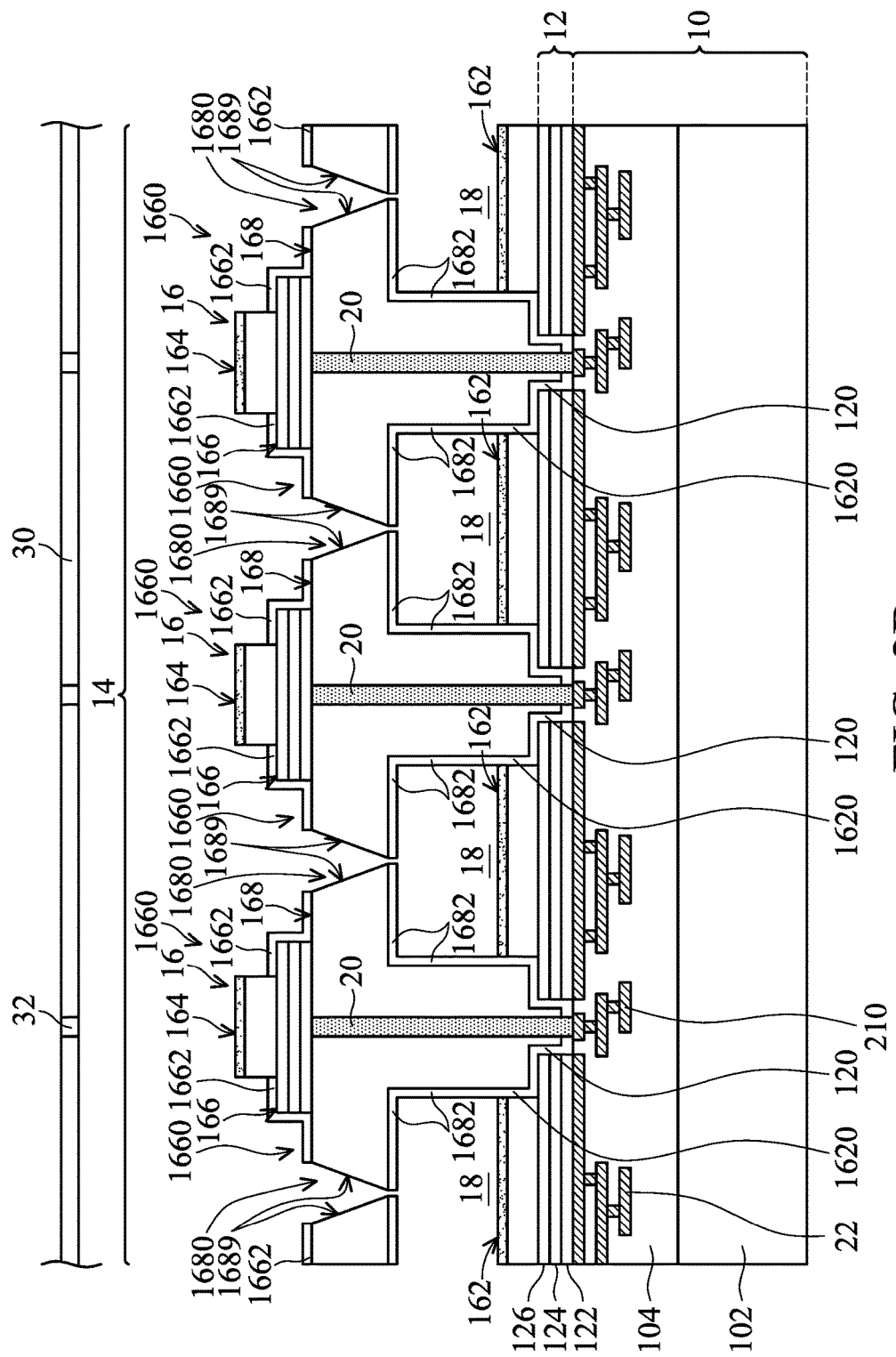
FIG. 2B is a cross-sectional view of a structure of an electrochemical unit in accordance with the fourth embodiment of the disclosure.

As shown in FIGS. 1B and 2B, the polymer layer 168 may be a T-shaped structure which is integrated and has the same material.

As shown in FIGS. 1A and 2A, the polymer layer 168 may comprise a vertical portion 1686 or a horizontal portion 1684. The horizontal portion 1684 is disposed above the vertical portion 1686. The horizontal portion 1684 is in contact with the second metal layer 166. The second metal layer 166 is in contact with the second electrode 164. The vertical portion 1686 is in contact with the first electrode 162, the first metal layer 12 and the substrate 10. The horizontal portion 1684 may comprise polymer materials, silicon oxide, silicon nitride or a multi-layered oxide/nitride film. The vertical portion 1686 may comprise silicon oxide, silicon nitride or a multi-layered oxide/nitride film. The pore 1680 is formed between the horizontal portions 1684 of the polymer layers 168 of every the two electrochemical cells 16.

As shown in FIGS. 1B and 2B, the polymer layer 168 may be a T-shaped structure which is integrated and has the same material. The polymer layer 168 may comprise a vertical portion or a horizontal portion (as shown in FIGS. 1A and 2A). The horizontal portion is disposed above the vertical portion. The horizontal portion is in contact with the second metal layer 166. The second metal layer 166 is in contact with the second electrode 164. The vertical portion is in contact with the first electrode 162, the first metal layer 12 and the substrate 10. The horizontal portion and the vertical portion may comprise polymer materials, silicon oxide, silicon nitride or a multi-layered oxide/nitride film. The pore 1680 is formed between the horizontal portions of the polymer layers 168 of every the two electrochemical cells 16.

The horizontal portion 1684 has a first end and a second end. The first end and the second end may be vertical planes 1688, as shown in FIGS. 1A and 1B, or the first end and the second end may be inclined planes 1689, as shown in FIGS. 2A and 2B.

In one embodiment, the first end and the second end of the horizontal portion 1684 may be the vertical planes 1688. In this embodiment, a circular pore may be constituted, as shown in FIGS. 1A and 1B. Other suitable shapes of the pore, for example, circular, triangle, square, rectangle, quadrilateral, pentagon or polygon, are also used in the disclosure.

In one embodiment, the inclined planes 1689 may be outwardly inclined from the upper portion to the lower portion of the first end and the second end. Optionally, in another embodiment, the inclined planes 1689 may be inwardly inclined from the upper portion to the lower portion of the first end and the second end. In such embodiments, a conical pore may be constituted, as shown in FIGS. 2A and 2B.

In one embodiment, a protection layer or a stop layer 1662 may be formed on the periphery of the second metal layer 166 to protect the polymer layer 168 and the second metal layer 166.

The circular pore 1680 formed by the vertical planes 1688 or the tapered conical pore 1680 formed by the inclined planes 1689 provide passing through of fine substances. Variation of impedance of solution caused by the fine substances in the solution is measured, and the characteristics of the fine substances are further distinguished. The diameter of the pore 1680 may be greater than or equal to 2 nm. The various diameters of the pore 1680 are designed in accordance with various fine substances, which are encompassed in the scope of the disclosure. Furthermore, each pair of the electrochemical cells 16 is able to measure variation of impedance of solution caused by variation of volume of the fine substances between the electrodes while the fine substances passes through the pore 1680, and the variation of impedance is presented on detection current. The relationship between the variation of the detection current and the volume of the fine substances are analyzed. If the volume and types of the substances are correlated, the types of the substances passing through the fine pore 1680 are further distinguished.

For example, chapter one of Allen J. Bard and Larry R. Faulkner, "Electrochemical Methods, Fundamentals and Applications" mentioned that a potential difference between two electrodes is described as $E_{appl}=E_{eq}+\eta-iR_s$. $E_{appl}$ is an applied potential, $E_{eq}$ is an equilibrium potential of an electrode relative to the other electrode, $\eta$ is a real overpotential provided to the electrodes, i is current, and $R_s$ is a resistance of solution. The above-mentioned potential and current have directivity. If $E_{eq}$ is regarded as a constant and $E_{appl}$ is a control factor, $\eta$ and i are altered with $R_s$. Therefore, i is described as $i=-(E_{appl}-E_{eq}-\eta)/R_s$. In the disclosure, a detectable parameter is current i, and the resistance of solution within the pore providing the fine substances to pass through is regarded as $R_s$. When the pores are occupied by the fine substances, the solution or the number of electrolytes within the pores are reduced, that is, conductive ions is fewer, so that the resistance $R_s$ of solution is increased, and the absolute value of current i is decreased. $R_s$ is regarded as a variable resistance. Based on this concept, a calibration curve of the volume of the fine substances relative to the absolute value of current is made. If the types and volume of the fin substances are correlated, the types of the substances are distinguished by the detection current.

Additionally, "Oxford NANOPORE Technologies" mentioned that when biomolecules of various sizes pass through nanopores, the variation of current can be measured. Furthermore, "NATURE NANOTECHNOLOGY|VOL 4|APRIL 2009 pp 265-270" mentioned that a current signal is measured when biomolecules pass through nanopores.

In one embodiment, the electrochemical cell 16 comprises an interconnection 20. The interconnection 20 is extended from the second electrode 164 and the second metal layer 166 to the substrate 10 to connect to a second internal circuit 210 through the polymer layer 168 and the first opening 120 of the first metal layer 12, and is further extended to connect to an external circuit or a circuit board (not shown). Therefore, in the disclosure, no external circuit connected to the second electrode is required. A first internal circuit 22 is extended from the first electrode 162 and the first metal layer 12 to the interior of the substrate 10, and is further extended to connect to the external circuit or the circuit board. The second internal circuit 210 and the first internal circuit 22 are separated. Therefore, no external circuit connected to the interconnection 20 is required. The distance between the first electrode 162 and the second electrode 164 is reduced due to the interconnection 20 located next to the cavity 18. The interconnection may be a through via. The first internal circuit 22 and the second internal circuit 210 may be an interconnection or a redistribution layer.

A cover 30 is disposed above the array 14 of the electrochemical cells. The cover 30 comprises an inlet 32 for injecting solution, for example a salt-containing electrolyte solution such as potassium chloride (KCl), etc., to the interior of the array 14 of the electrochemical cells.

If the fine substances are charged (positive charge or negative charge), the fine substances are conducted into the interior of the electrochemical cells 16 through an electric field formed between the first electrode 162 and the second electrode 164. However, if the fine substances are neutral, the fine substances enter the interior of the electrochemical cells 16 through diffusion of molecular motion.

The inlet 32 may be sealed after a suitable amount of solution is injected, such as plugging or filling glue, etc.

Referring to FIGS. 3A-3F, which are cross-sectional views of manufacture method of an electrochemical unit in accordance with the first embodiment of the disclosure, the steps of the manufacture method of an electrochemical unit of the disclosure comprise providing a substrate 10, and forming an array 14 of electrochemical cells on the substrate 10. The steps of forming each of the electrochemical cells 16 comprise forming a plurality of first electrodes 162 on the substrate 10, forming a polymer layer 168 on the first electrodes 162 and the substrate 10, and forming a second electrode 164 on the polymer layer 168. An interconnection 20 is formed and respectively connected to the second electrode 164 and a circuit or a circuit board (not shown) through the polymer layer 168 and a second internal circuit 210 within the substrate 10. A first internal circuit 22 is formed and respectively connected to the first electrode 162 and the circuit or the circuit board through the interior of the substrate 10. The second internal circuit 210 and the first internal circuit 22 are separated. A cover 30 is disposed above the electrochemical cells 16. A solution is injected into the interior of the electrochemical cells 16. A pore 1680 is formed between the polymer layers 168 of every the two electrochemical cells 16. The pore 1680 provides passing through of fine substances. Variation of impedance of solution caused by the fine substances in the solution is measured, and the characteristics of the fine substances are further distinguished.

Figure 3A:
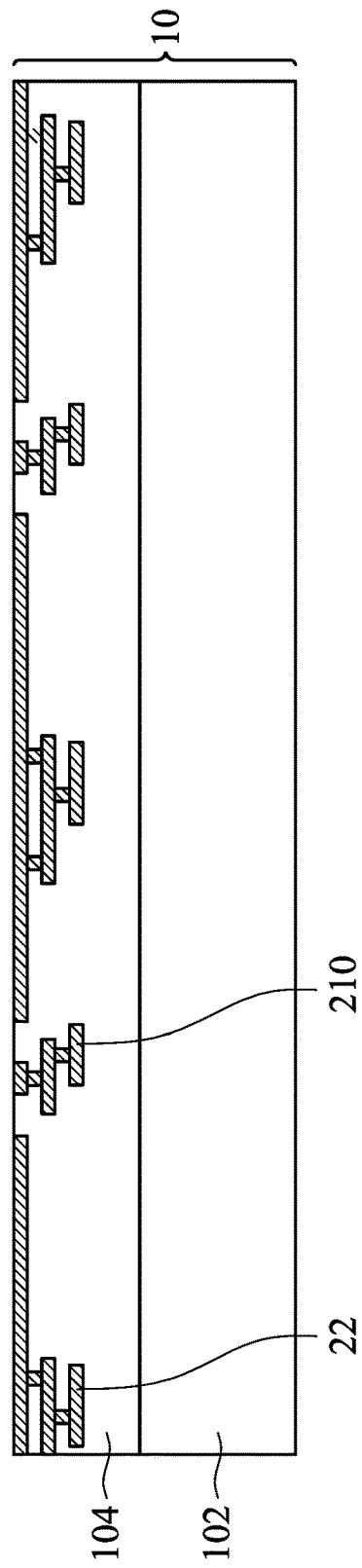
FIGS. 3A-3F are cross-sectional views of manufacture method of an electrochemical unit in accordance with the first embodiment of the disclosure.

As shown in FIG. 3A, which is a cross-sectional view of the manufacture method of an electrochemical unit in accordance with the first embodiment of the disclosure, the steps thereof comprise providing a substrate 10. Specifically, the substrate 10 comprises a silicon substrate 102, an oxide layer (or a nitride layer) 104 having metal wires and active components, the first internal circuit 22 subsequently connected to the first electrode 162, and the second internal circuit 210 subsequently connected to the second electrode 164.

Figure 3B:
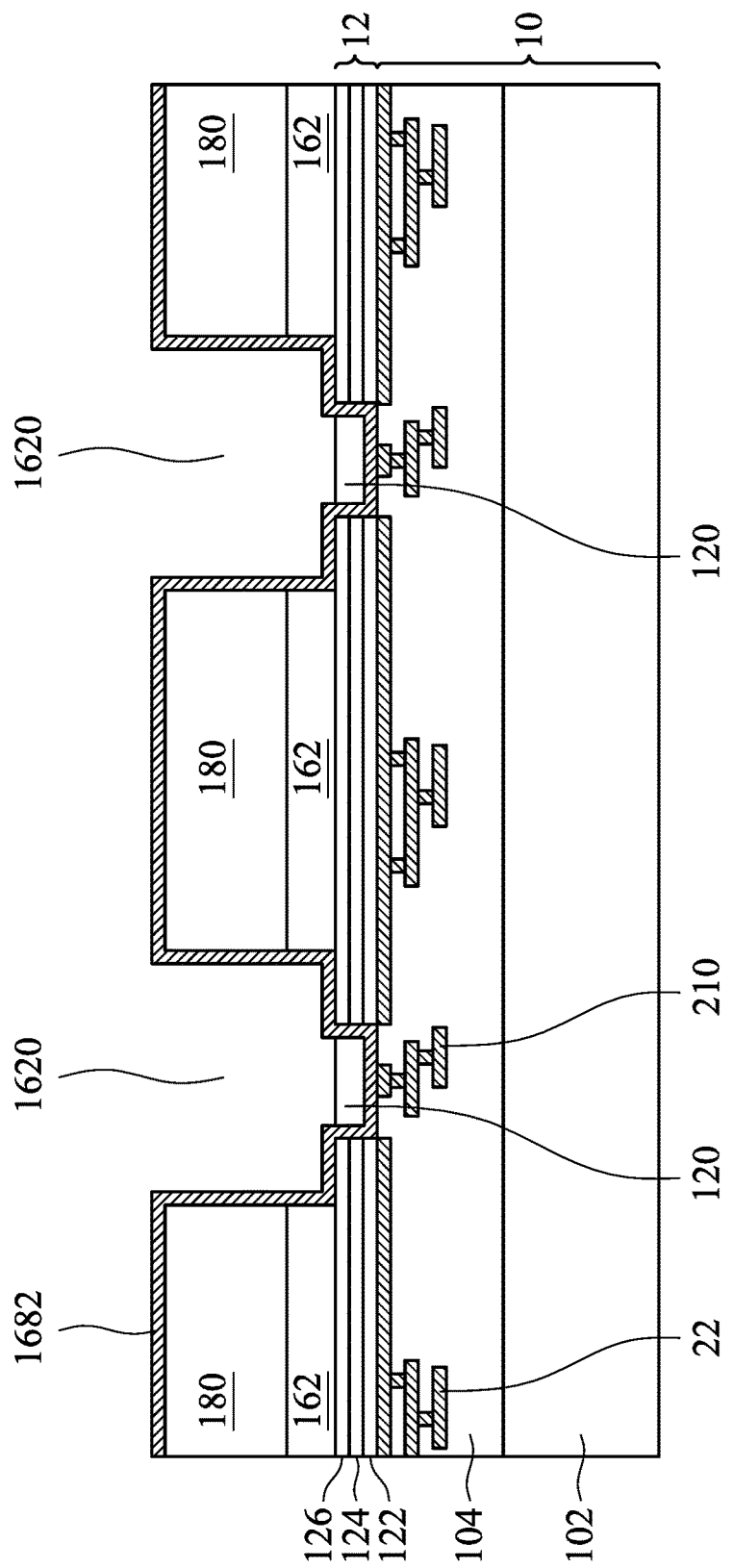

As shown in FIG. 3B, a first metal layer 12 is formed on the substrate 10. The first metal layer 12 may comprise, for example, a multi-layered film of titanium, copper and gold, and is formed by sputtering or chemical vapor deposition.

In one embodiment, the first metal layer 12 may comprise chromium/nickel (Cr/Ni), chromium/gold (Cr/Au), titanium/copper (Ti/Cu), nickel/gold (Ni/Au), chromium/nickel/gold (Cr/Ni/Au), titanium/copper/gold (Ti/Cu/Au) or titanium/gold (Ti/Au).

The location of the first electrode 162 above the first metal layer 12 is defined using a photoresist. Silver is electroplated on the first metal layer 12, and the silver is chlorinated to form silver chloride, such that the silver/silver chloride (Ag/AgCl) is formed on the first metal layer 12 to form the first electrode 162.

Next, a sacrificial layer 180 is formed on the silver/silver chloride (the first electrode 162). The sacrificial layer 180 may comprise polymers or metal. After the sacrificial layer 180 is formed and the photoresist is removed, a plurality of openings 1620 between the adjacent sacrificial layers 180 and the adjacent first electrodes 162 are formed, exposing the first metal layer 12 at the bottom of the opening 1620.

The first metal layer 12 at the bottom of the opening 1620 is etched by, for example wet etching, to form a first opening 120, exposing the substrate 10, such that the first metal layers 12 adjacent to the bottom of the opening 1620 are separated to isolate the adjacent first electrodes 162, and the first electrodes 162 of each of the electrochemical cells 16 of the array 14 of the electrochemical cells are independent. The size of the opening 1620 is larger than the size of the first opening 120. Or the size of the opening 1620 is equal to the size of the first opening 120.

In one embodiment, a protection layer or a stop layer 1682 is formed on the first electrodes 162, the first metal layers 12 and substrate 10 of the inner peripheral walls of the openings 1620 and the first openings 120, and on the sacrificial layer 180 to protect the polymer layer 168 and the sidewalls thereof. The protection layer 1682 may be a nitride layer.

Figure 3C:
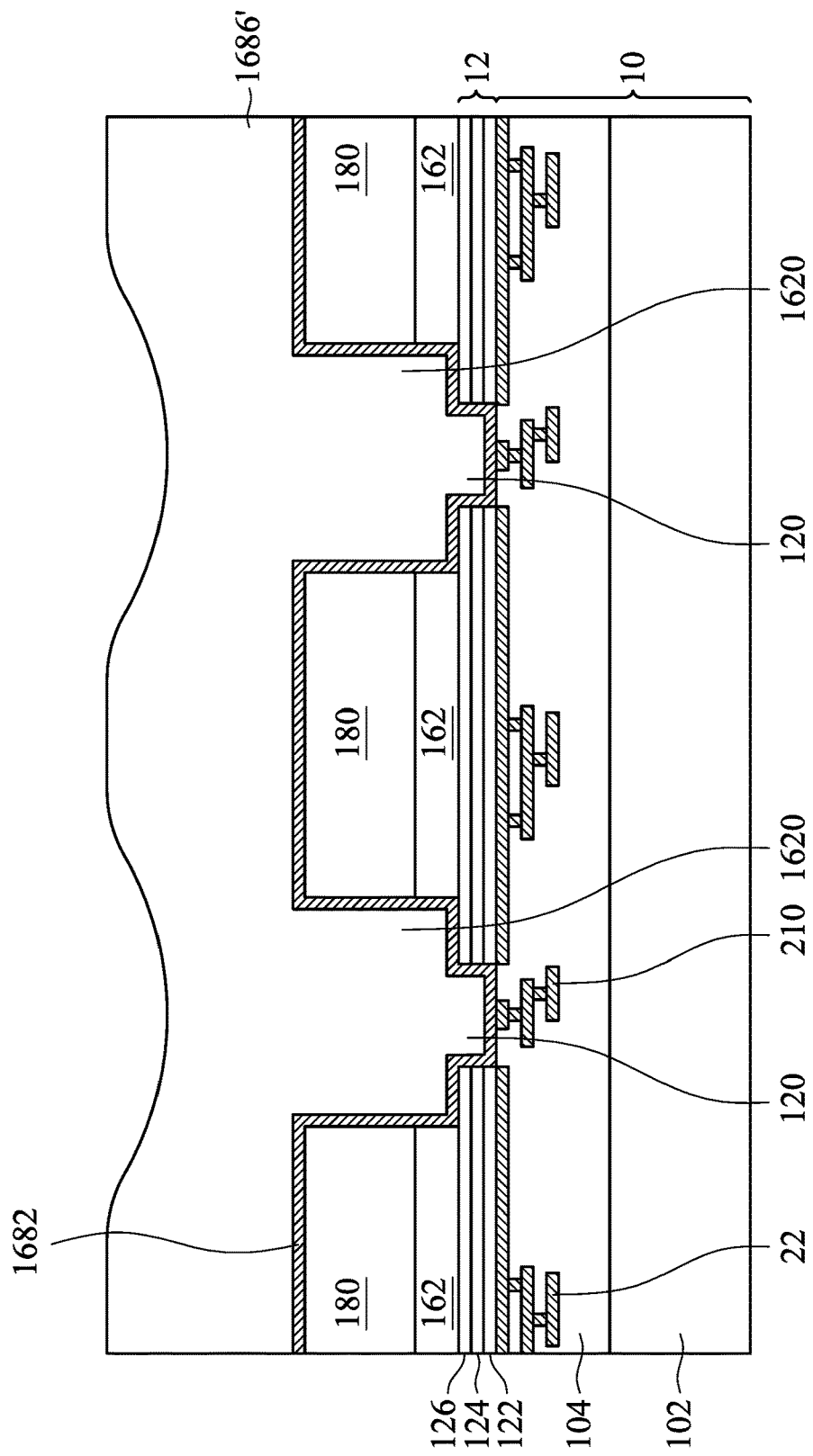

As shown in FIG. 3C, a nitride layer, an oxide layer or a multi-layered oxide/nitride film 1686' (vertical portion) or 168 (horizontal portion and vertical portion) is filled into the openings 1620 and the first openings 120, and overlies the sacrificial layer 180 by chemical vapor deposition (CVD). In one embodiment, an oxide layer may be selected.

Figure 3D:
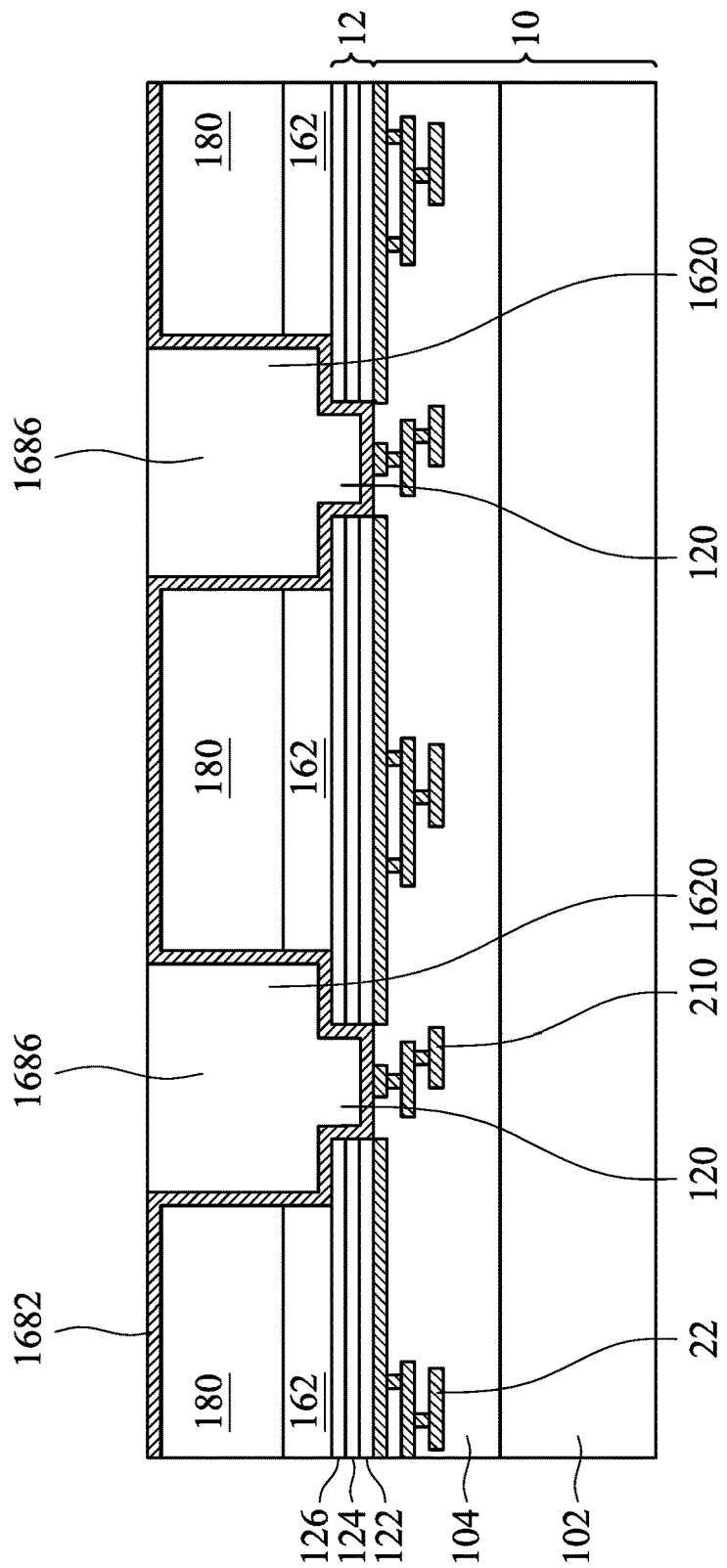

As shown in FIG. 3D, next, the oxide layer or the nitride layer 1686' is polished by chemical mechanical planarization (CMP), exposing the sacrificial layer 180 and the vertical portion 1686. If the protection layer 1682 is disposed on the sacrificial layer 180, the oxide layer or the nitride layer 1686' is polished to the protection layer 1682.

Figure 3E:
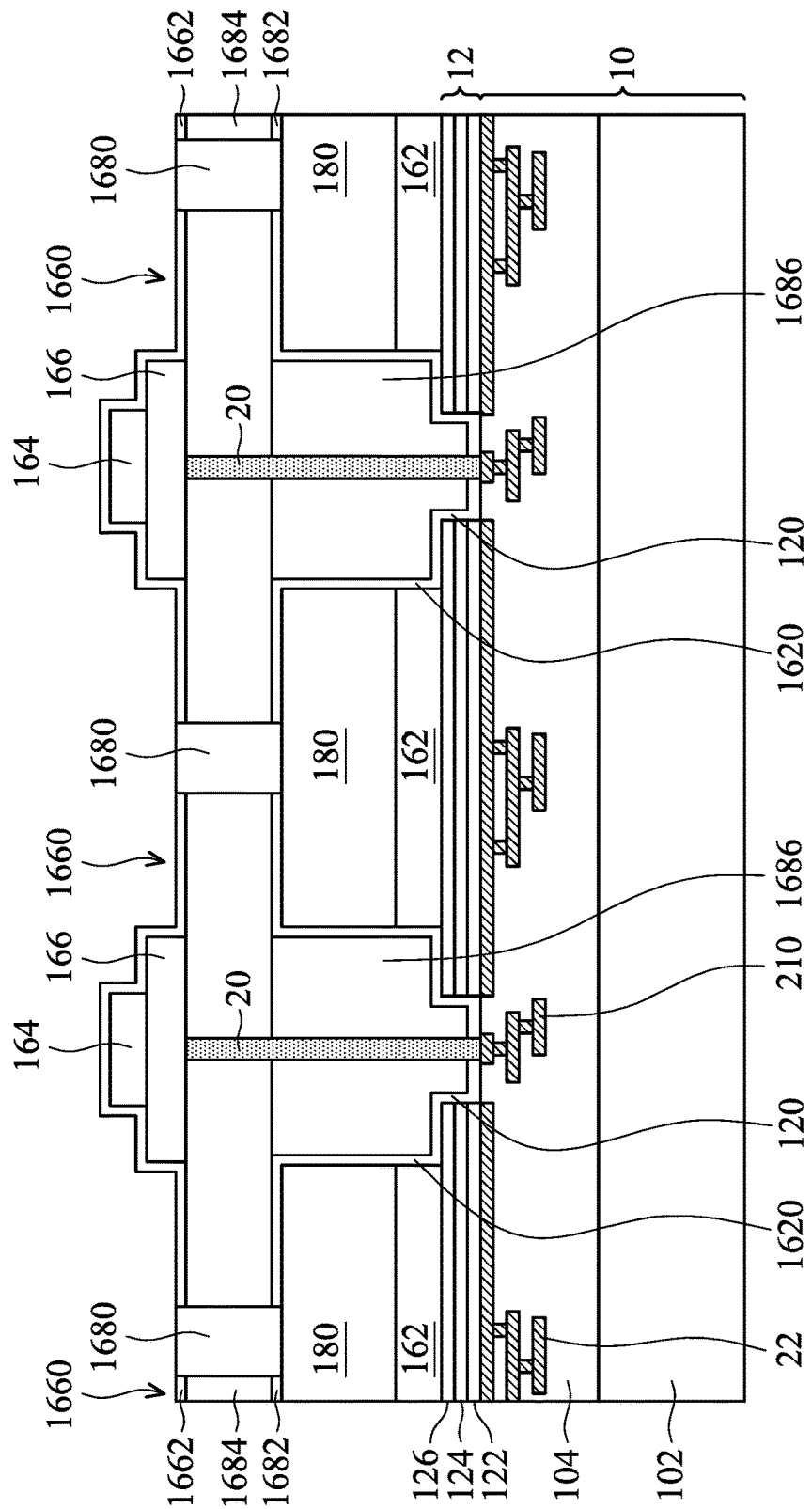

As shown in FIG. 3E, a polymer layer 1684 (horizontal portion) is formed on the sacrificial layer 180 and the vertical portion 1686 (or the protection layer) by spin coating.

As shown in FIG. 3E, a via is formed through the polymer layer 1684 to the substrate 10 by laser drilling or etching, and a conductive material is filled into the via to form the interconnection (through via) 20 to connect to the second internal circuit 210 of the substrate 10.

A second metal layer 166 is formed on the polymer layer 1684 by sputtering, chemical vapor deposition or electroless plating.

After the location of the second electrode 164 is defined using a photoresist, silver is electroplated, and the silver is chlorinated to form silver chloride, such that the silver/silver chloride (Ag/AgCl) is formed on the second metal layer 166 to form the second electrode 164.

In one embodiment, the second metal layer 166 may comprise chromium/nickel (Cr/Ni), chromium/gold (Cr/Au), titanium/copper (Ti/Cu), nickel/gold (Ni/Au), chromium/nickel/gold (Cr/Ni/Au), titanium/copper/gold (Ti/Cu/Au) or titanium/gold (Ti/Au), etc. After the second electrode 164 is formed, the photoresist is removed.

The second metal layer 166 below the second electrode 164 is etched by, for example wet etching, such that the adjacent second metal layers 166 below the second electrodes 164 are separated to isolate the adjacent second electrodes 164.

In one embodiment, a nitride layer is formed by chemical vapor deposition (CVD). That is, the nitride layer, a protection layer or a stop layer 1662, is formed on the second metal layers 166, the second electrodes 164 and the polymer layer 1684.

The location of the pore 1680 (via) above the nitride layer 1662 is defined using a photoresist. The nitride layer 1662 and the polymer layer 1684 are then etched through by, for example dry etching, etc., to form the circular pore 1680. The photoresist is then removed.

Figure 3F:
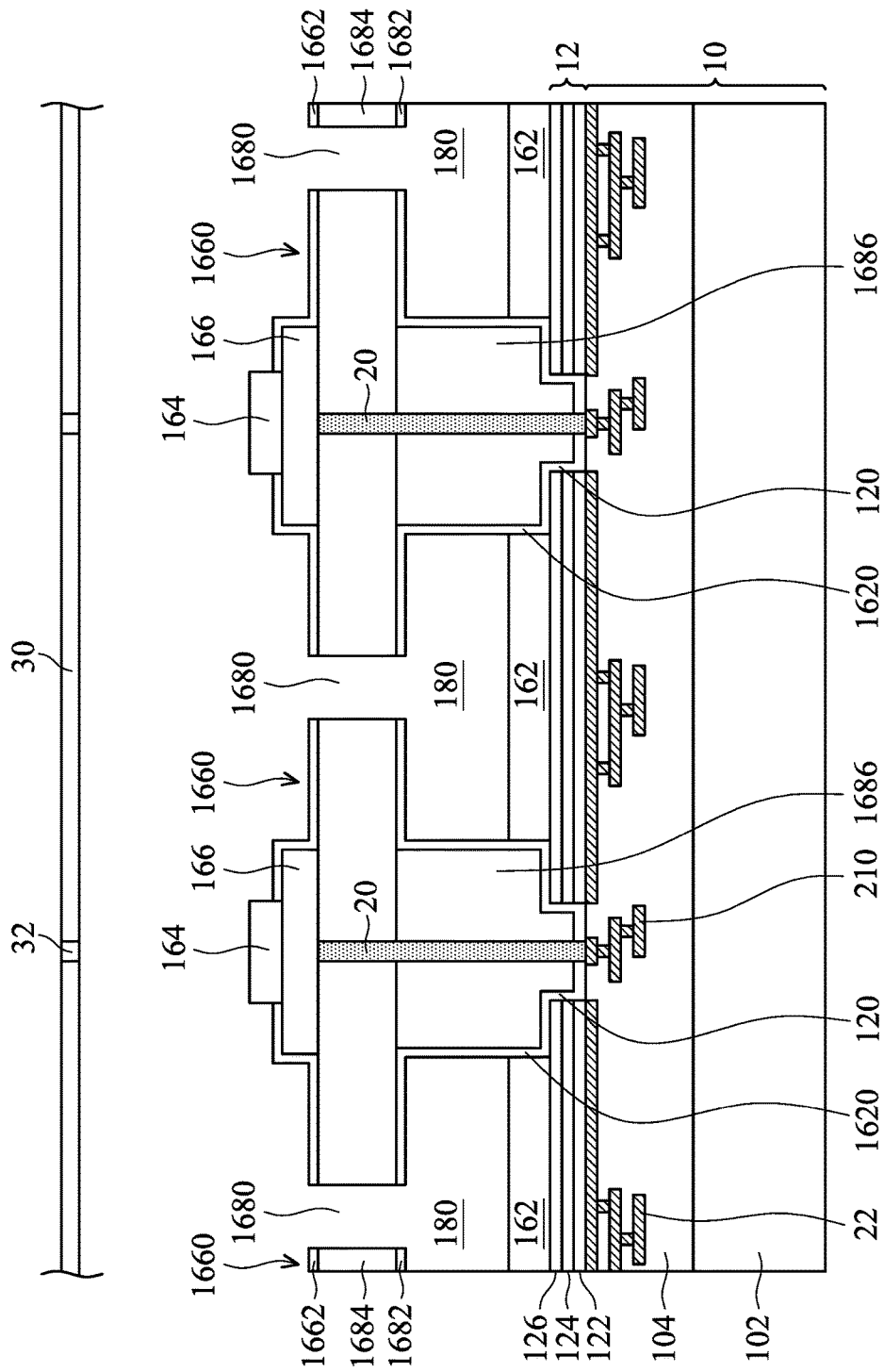
Figure 4A:
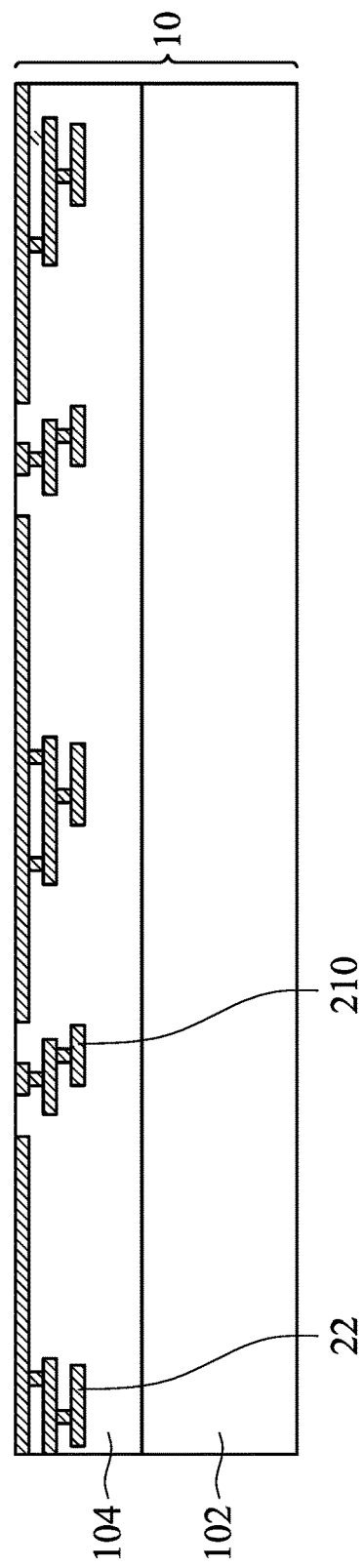
FIGS. 4A-4F are cross-sectional views of manufacture method of an electrochemical unit in accordance with the second embodiment of the disclosure.
Figure 4B:
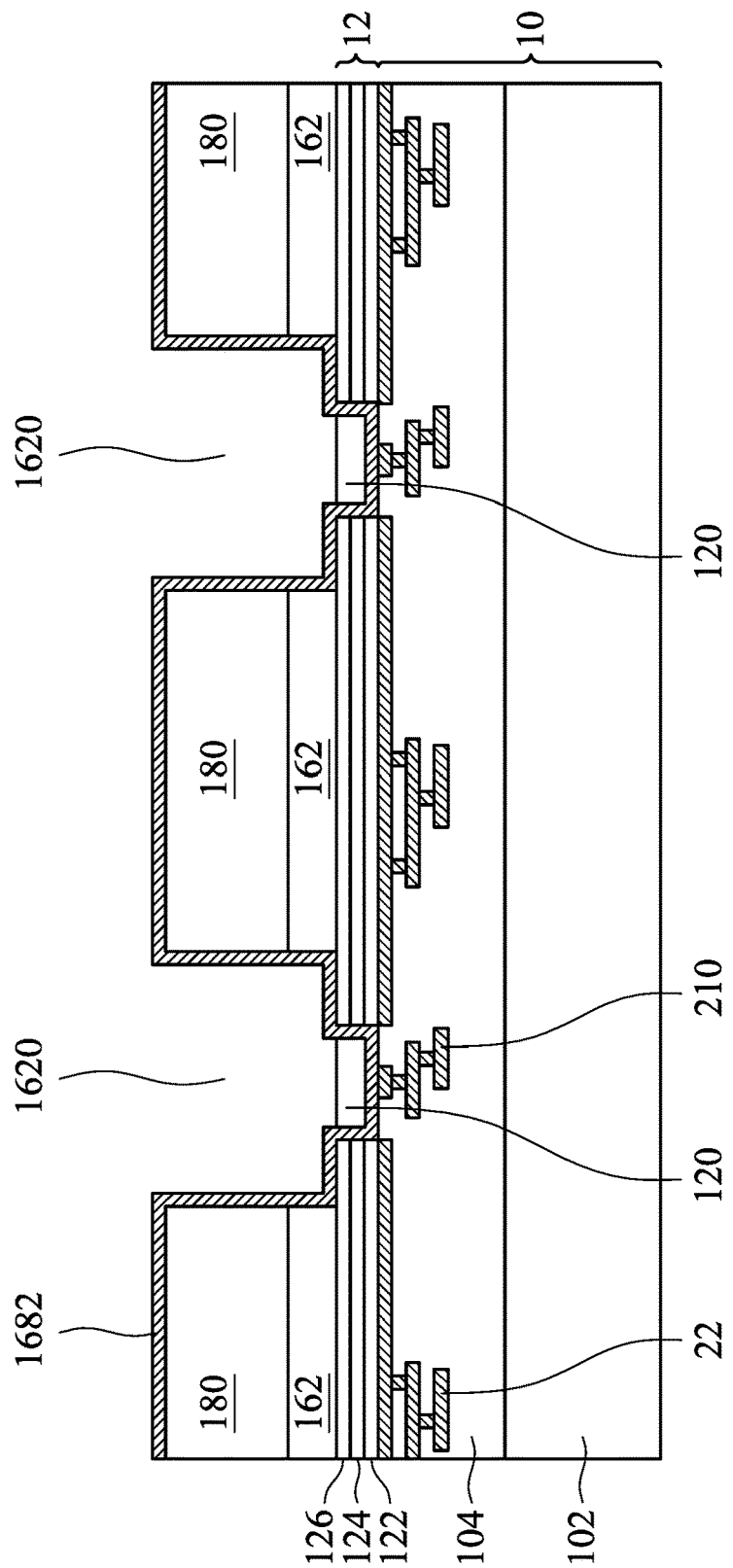
Figure 4C:
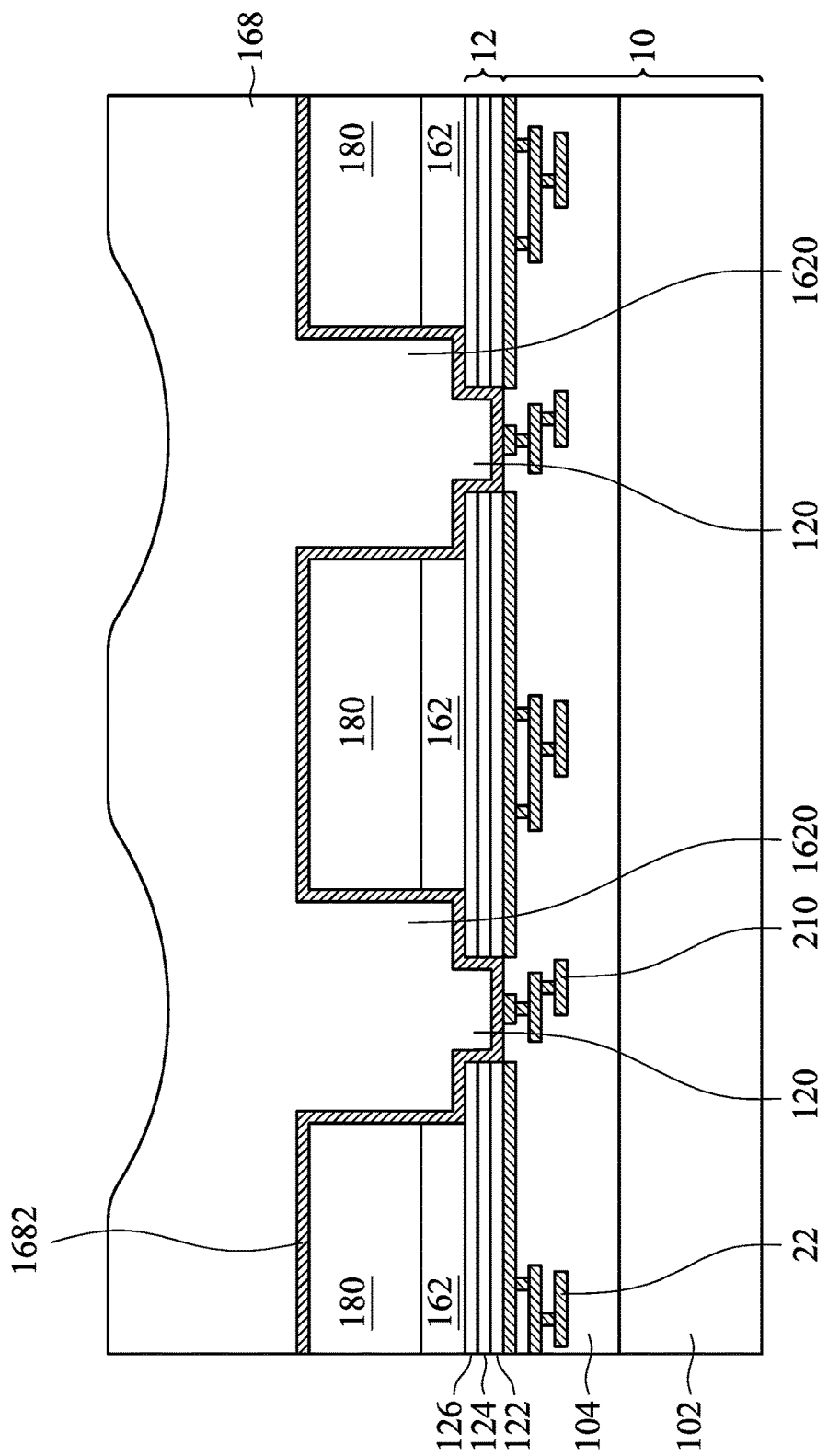
Figure 4D:
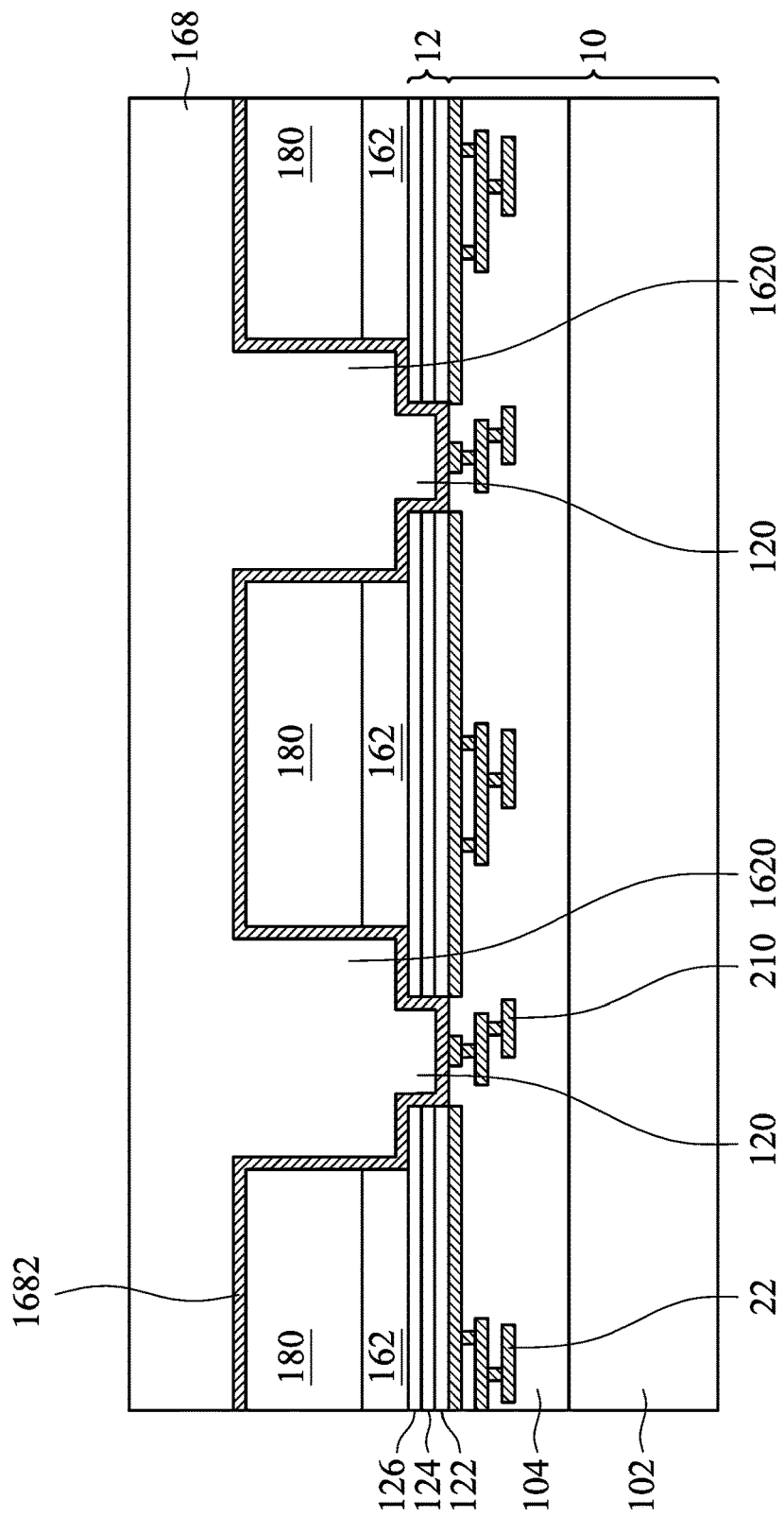
Figure 4E:
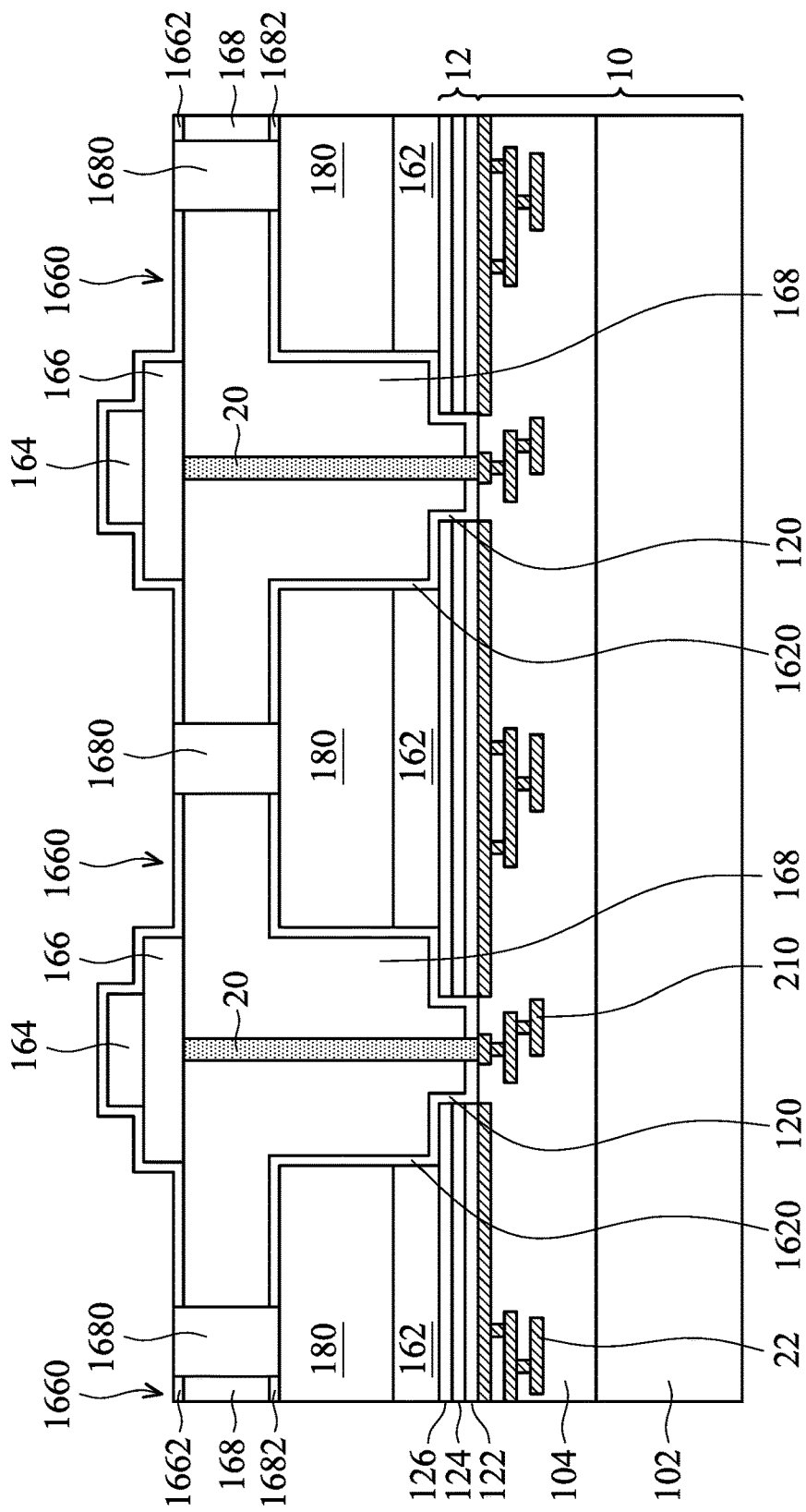
Figure 4F:
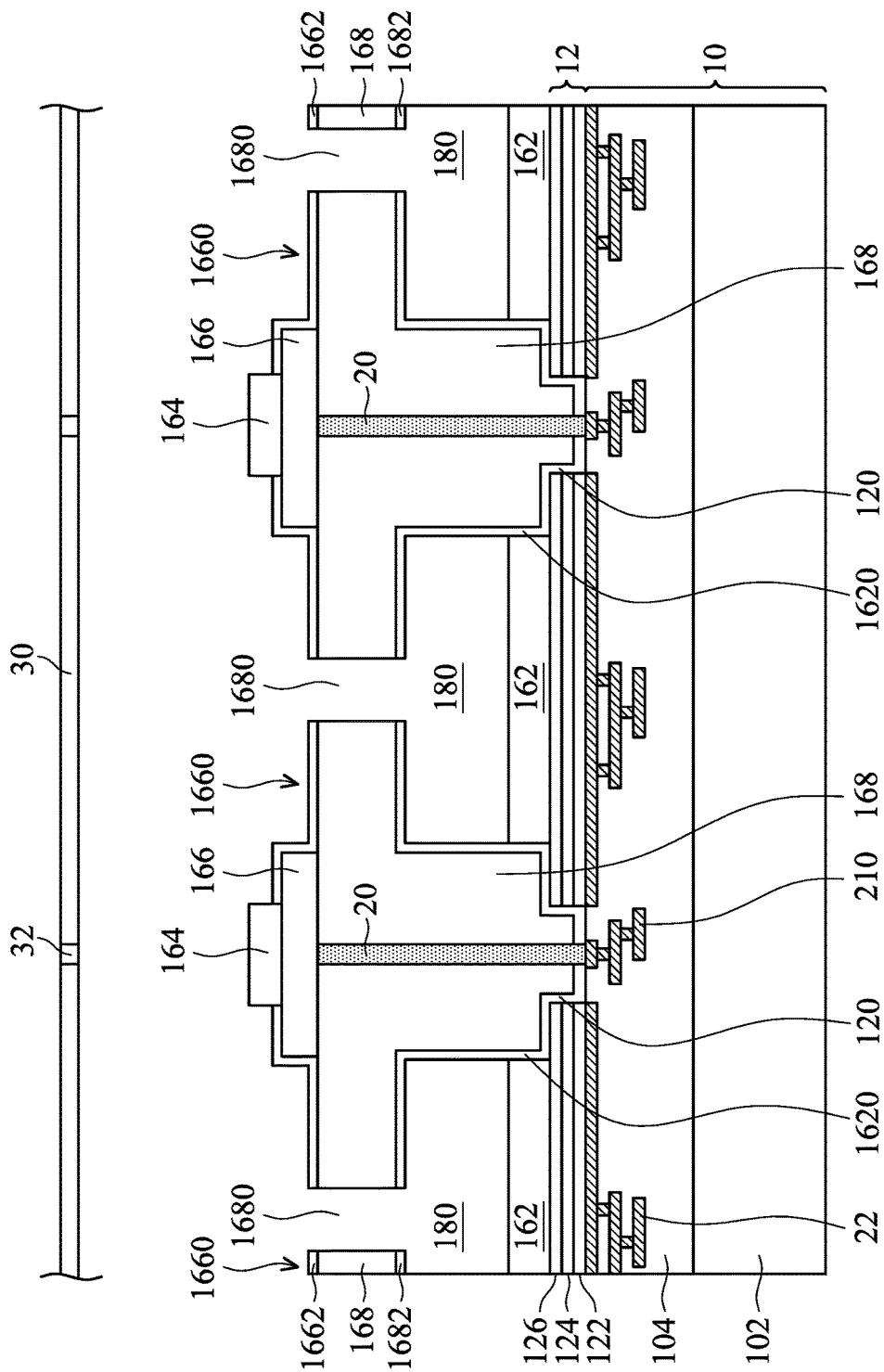

As shown in FIG. 3F, the sacrificial layer 180 is removed using an organic or inorganic solution.

The nitride layer 1662 covering the second electrode 164 is etched using a diluted hydrofluoric acid (DHF) solution, exposing the second electrode 164.

A cover 30 is formed above the array 14 of the electrochemical cells.

A solution, for example a salt-containing electrolyte solution such as potassium chloride (KCl), etc., is injected into the interior of the array 14 of the electrochemical cells through an inlet 32 of the cover 30, and then the inlet 32 is sealed.

The first embodiment of the manufacture method of an electrochemical unit of the disclosure is corresponded to FIG. 1A. FIG. 2A is also corresponded to a similar manufacture method. The distinction therebetween is that, in FIG. 3E, the location of the pore 1680 (via) above the nitride layer 1662 is defined using a photoresist. The nitride layer 1662 and the polymer layer 1684 are then etched through by, for example dry etching, etc., to form the conical pore 1680. The photoresist is then removed.

Referring to FIGS. 4A-4F, which are cross-sectional views of manufacture method of an electrochemical unit in accordance with the second embodiment of the disclosure, the manufacture method of an electrochemical unit of the second embodiment is similar to that of the first embodiment of the disclosure. The distinction therebetween is that, in FIG. 4D, the multi-layered oxide/nitride film 168 is continuously polished to a height above the sacrificial layer by chemical mechanical planarization after the multi-layered oxide/nitride film 168 is planarized. The thickness of the oxide layer or the nitride layer above the sacrificial layer is decided by light or sonar measurements. Other similar steps are not repeated.

In summary, the cells of the structure of the electrochemical unit of the disclosure are arranged to form an array. Each of the cells is equipped with exclusive first and second electrodes of silver/silver chloride, and a fine pore is constituted between the first and second electrodes. Each of the cells is able to respectively measure variation of impedance of solution caused by variation of volume of fine substances between the electrodes while the fine substances passes through the fine pore, and the variation of impedance is presented on variation of detection current. The relationship between the variation of the detection current and the volume of the fine substances are analyzed. If the volume and types of the substances are correlated, the types of the substances passing through the fine pore are further distinguished.

Additionally, in the disclosure, the second electrode is integrated into the electrochemical cell such that inconsistency of potential drop caused by solution between the second electrode (an external electrode) and a plurality of internal electrodes (the first electrodes) is improved. Simultaneously, the distance between the first electrode (an internal electrode) and the second electrode (an external electrode) is shortened, improving potential drop caused by an electrolyte solution and increasing electric current resulted from electrode field. Furthermore, poor bonding and alignment error caused by a bonding procedure in processes is also improved. Moreover, the protection layer or the stop layer is formed around the cavity, increasing selection of materials of the cavity.

Summary, the disclosure is to arrange cells of an electrochemical unit to form an array. Each of the cells is equipped with exclusive first and second electrodes of silver/silver chloride, and a fine pore is constituted between the first and second electrodes. Each of the cells is able to respectively measure variation of impedance of solution caused by variation of volume of fine substances between the electrodes while the fine substances passes through the fine pore, and the variation of impedance is presented on variation of detection current. The relationship between the variation of current and the volume of the fine substances are analyzed. If the volume and types of the substances are correlated, the types of the substances passing through the fine pore are further distinguished.

The disclosure is to integrate the second electrode into the electrochemical cell such that inconsistency of potential drop caused by solution between the second electrode (an external electrode) and a plurality of internal electrodes (the first electrodes) is improved.

The disclosure is to shorten the distance between the first electrode (an internal electrode) and the second electrode (an external electrode), improving potential drop caused by an electrolyte solution.

The disclosure is to improve poor bonding and alignment error caused by a bonding procedure in processes.

The disclosure is to form a protection layer or a stop layer around a cavity, increasing selection of materials of the cavity.

It will be apparent to those skilled in the art that various modifications and variations can be made to the disclosed embodiments. It is intended that the specification and examples be considered as exemplary only, with the true scope of the disclosure being indicated by the following claims and their equivalents.

What is claimed is:

1. A structure of an electrochemical unit, comprising:
    a substrate;
    a first metal layer disposed on the substrate; and
    an array of electrochemical cells disposed on the first metal layer, wherein the array of the electrochemical cells comprises a plurality of electrochemical cells, and each of the electrochemical cells comprises:
    the first metal layer disposed on the substrate;
    a first electrode disposed on the first metal layer;
    a polymer layer disposed on the substrate and adjacent to the first metal layer and the first electrode, wherein a pore is constituted between the polymer layers of every the two electrochemical cells, and a cavity located above the first electrode is defined between every the two electrochemical cells, wherein the cavity is communicated with the pore;
    a second metal layer disposed on the polymer layer; and
    a second electrode disposed on the second metal layer.

2. The structure of the electrochemical unit as claimed in claim 1, wherein the first electrode and the second electrode are silver/silver chloride.

3. The structure of the electrochemical unit as claimed in claim 1, further comprising a protection layer formed on walls of the polymer layers located at the periphery of the cavity.

4. The structure of the electrochemical unit as claimed in claim 3, wherein the polymer layers are a T-shaped structure comprising a vertical portion and a horizontal portion disposed above the vertical portion, the horizontal portion is in contact with the second metal layer, the second metal layer is in contact with the second electrode, the vertical portion is in contact with the first electrode, the first metal layer and the substrate, and the pore is constituted between the horizontal portions of the polymer layers of every the two electrochemical cells.

5. The structure of the electrochemical unit as claimed in claim 4, wherein the horizontal portion has a first end and a second end which are vertical planes, and a pore is constituted between the first end and the second end of every two T-shaped structures, wherein the pore has a shape of circular, triangle, square, rectangle, quadrilateral, pentagon or polygon.

6. The structure of the electrochemical unit as claimed in claim 4, wherein the horizontal portion has a first end and a second end which are inclined planes, and a conical pore is constituted between the first end and the second end.

7. The structure of the electrochemical unit as claimed in claim 4, wherein the horizontal portion comprises polymer materials, silicon oxide, silicon nitride or a multi-layered film, and the vertical portion comprises silicon oxide, silicon nitride or a multi-layered film.

8. The structure of the electrochemical unit as claimed in claim 1, wherein the substrate comprises a silicon substrate and an oxide layer or a nitride layer having metal wires and active components disposed on the silicon substrate.

9. The structure of the electrochemical unit as claimed in claim 1, wherein the first metal layer and the second metal layer comprise a stack of titanium, copper and gold, wherein the titanium is in contact with an oxide layer or a nitride layer of the substrate, or the first metal layer and the second metal layer comprising chromium/nickel, chromium/gold, titanium/copper, nickel/gold, chromium/nickel/gold, titanium/copper/gold or titanium/gold.

10. The structure of the electrochemical unit as claimed in claim 1, wherein the polymer layer is disposed in an opening between the first electrodes and in a first opening between the first metal layers, and adjacent to the first metal layer and the first electrode.

11. The structure of the electrochemical unit as claimed in claim 10, wherein the polymer layer comprises polymer materials, silicon oxide, silicon nitride or a multi-layered film.

12. The structure of the electrochemical unit as claimed in claim 1, wherein the second metal layer comprises a stack of titanium, copper and gold, and comprises a plurality of second openings, wherein the titanium is in contact with the polymer layer and the gold is in contact with the second electrode.

13. The structure of the electrochemical unit as claimed in claim 1, further comprising a first internal circuit extending from the first electrode and the first metal layer to the interior of the substrate, and further extending to connect to an external circuit or a circuit board.

14. The structure of the electrochemical unit as claimed in claim 13, wherein the electrochemical cell further comprises an interconnection extending from the second electrode and the second metal layer to a second internal circuit within the substrate through the polymer layer and a first opening of the first metal layer, and further extending to connect to the external circuit or the circuit board, wherein the first internal circuit and second internal circuit are separated.

15. A manufacture method of an electrochemical unit, comprising:
    providing a substrate; and
    forming an array of electrochemical cells on the substrate, wherein the array of the electrochemical cells comprises a plurality of electrochemical cells, and the steps comprise:
    forming a first metal layer on the substrate;
    forming a plurality of first electrodes on the first metal layer;
    forming a polymer layer on the substrate and adjacent to the first metal layer and the first electrodes, wherein a pore is constituted between the polymer layers of every the two electrochemical cells, and a cavity located above the first electrode is defined between every the two electrochemical cells, wherein the cavity is communicated with the pore;
    forming a second metal layer on the polymer layer; and
    forming a second electrode on the second metal layer.

16. The manufacture method of an electrochemical unit as claimed in claim 15, further comprising forming an interconnection respectively connected to the second electrode and an external circuit or a circuit board through the polymer layer and a second internal circuit within the substrate; and forming a first internal circuit respectively connected to the first electrode and the external circuit or the circuit board through the interior of the substrate, wherein the first internal circuit and the second internal circuit are separated.

17. The manufacture method of an electrochemical unit as claimed in claim 15, further comprising forming a cover above the electrochemical cells, and filling a solution into the interior of the electrochemical cells.

18. The manufacture method of an electrochemical unit as claimed in claim 15, wherein the substrate comprises a silicon substrate, an oxide layer or a nitride layer having metal wires and active components, a first internal circuit subsequently connected to the first electrode, and a second internal circuit subsequently connected to the second electrode.

19. The manufacture method of an electrochemical unit as claimed in claim 15, wherein a first metal layer is formed on the substrate by sputtering or chemical vapor deposition.

20. The manufacture method of an electrochemical unit as claimed in claim 19, wherein the location of the first electrode above the first metal layer is defined using a photoresist, silver is electroplated on the first metal layer, and the silver is chlorinated to form silver chloride, such that the silver/silver chloride is formed on the first metal layer to form the first electrode.

21. The manufacture method of an electrochemical unit as claimed in claim 20, wherein a sacrificial layer is formed on the first electrode, and a plurality of openings are formed between the adjacent sacrificial layers and the adjacent first electrodes after the photoresist is removed, exposing the first metal layer at the bottom of the opening.

22. The manufacture method of an electrochemical unit as claimed in claim 21, wherein the sacrificial layer comprises polymers or metal.

23. The manufacture method of an electrochemical unit as claimed in claim 21, wherein the first metal layer at the bottom of the opening is etched to form a first opening, exposing the substrate, such that the first metal layers adjacent to the bottom of the opening are separated to isolate the adjacent first electrodes, and the first electrodes of each of the electrochemical cells of the array of the electrochemical cells are independent.

24. The manufacture method of an electrochemical unit as claimed in claim 23, wherein a protection layer or a stop layer is formed on inner peripheral walls of the openings and the first openings and on the sacrificial layer.

25. The manufacture method of an electrochemical unit as claimed in claim 24, wherein a nitride layer or an oxide layer is filled into the openings and the first openings and overlies the sacrificial layer by chemical vapor deposition.

26. The manufacture method of an electrochemical unit as claimed in claim 25, wherein the nitride layer or the oxide layer is polished by chemical mechanical planarization, exposing the sacrificial layer and the nitride layer or the oxide layer.

27. The manufacture method of an electrochemical unit as claimed in claim 25, wherein the nitride layer or the oxide layer is continuously polished to a height above the sacrificial layer by chemical mechanical planarization after the nitride layer or the oxide layer is planarized.

28. The manufacture method of an electrochemical unit as claimed in claim 26, wherein the polymer layer is formed on the sacrificial layer and the nitride layer or the oxide layer by chemical vapor deposition or spin coating.

29. The manufacture method of an electrochemical unit as claimed in claim 27, wherein a via is formed through the polymer layer to the substrate by laser drilling or etching, and a conductive material is filled into the via to connect to a second internal circuit.

30. The manufacture method of an electrochemical unit as claimed in claim 29, wherein a second metal layer is formed on the polymer layer by sputtering, chemical vapor deposition or electroless plating, after the location of the second electrode of the electrochemical cell is defined using a photoresist, silver is electroplated, and the silver is chlorinated to form silver chloride, such that the silver/silver chloride is formed on the second metal layer to form the second electrode.

31. The manufacture method of an electrochemical unit as claimed in claim 30, wherein the second metal layer below the second electrode is etched to form a second opening, such that the adjacent second metal layers below the second electrodes are separated to isolate the adjacent second electrodes.

32. The manufacture method of an electrochemical unit as claimed in claim 31, wherein a nitride layer is formed on the second metal layers, the second electrodes and the polymer layer by chemical vapor deposition.

33. The manufacture method of an electrochemical unit as claimed in claim 32, wherein a location of the pore above the nitride layer is defined using a photoresist, and the nitride layer and the polymer layer are etched through to form the pore.

34. The manufacture method of an electrochemical unit as claimed in claim 33, wherein the sacrificial layer is removed using an organic or inorganic solution.

35. The manufacture method of an electrochemical unit as claimed in claim 34, wherein the nitride layer covering the second electrode is etched using a diluted hydrofluoric acid solution, exposing the second electrode.

36. The manufacture method of an electrochemical unit as claimed in claim 15, further comprising forming a cover above the array of the electrochemical cells, and filling a solution into the interior of the array of the electrochemical cells.

37. The manufacture method of an electrochemical unit as claimed in claim 36, wherein the solution is a salt-containing electrolyte solution.

* * * * *